(12) United States Patent
Pierce et al.

(10) Patent No.: US 7,906,024 B2
(45) Date of Patent: Mar. 15, 2011

(54) SHEAR PROTECTANTS IN HARVEST MICROFILTRATION

(75) Inventors: James Pierce, Celbridge (IE); Enda Moran, Blessington (IE)

(73) Assignee: Wyeth Research Ireland Limited, Newbridge (IE)

( * ) Notice: Subject to any disclaimer, the term of this patent is extended or adjusted under 35 U.S.C. 154(b) by 1412 days.

(21) Appl. No.: 11/338,214

(22) Filed: Jan. 24, 2006

(65) Prior Publication Data

US 2006/0194313 A1     Aug. 31, 2006

Related U.S. Application Data

(60) Provisional application No. 60/647,184, filed on Jan. 25, 2005.

(51) Int. Cl.
*B01D 61/00*     (2006.01)

(52) U.S. Cl. ........ 210/639; 210/651; 210/805; 435/325; 435/404; 530/350; 530/412; 530/414; 536/25.4

(58) Field of Classification Search .................. 210/639, 210/649–651, 194, 195.2, 805; 530/333, 530/344, 350, 412, 414; 514/2, 12–14; 536/25.4; 435/404, 431, 325
See application file for complete search history.

(56) References Cited

U.S. PATENT DOCUMENTS

| | | | |
|---|---|---|---|
| 4,707,542 A * | 11/1987 | Friedman et al. ............. 530/371 |
| 4,751,003 A * | 6/1988 | Raehse et al. ................. 210/639 |
| 5,336,603 A * | 8/1994 | Capon et al. ................. 435/69.7 |
| 5,484,531 A * | 1/1996 | Kuehne et al. ................ 210/653 |
| 5,597,486 A * | 1/1997 | Lutz .............................. 210/639 |
| 5,681,746 A * | 10/1997 | Bodner et al. ................ 435/350 |
| 5,804,420 A | 9/1998 | Chan et al. |
| 6,245,568 B1 * | 6/2001 | Volkin et al. ...................... 436/8 |
| 6,436,897 B2 * | 8/2002 | Danko et al. ...................... 514/2 |
| 6,607,784 B2 * | 8/2003 | Kipp et al. ................. 427/213.3 |
| 7,270,990 B2 * | 9/2007 | Williams et al. ............. 435/239 |
| 7,314,746 B2 * | 1/2008 | Au-Yeung et al. ........... 435/239 |
| 7,332,571 B2 * | 2/2008 | Miao et al. .................... 530/333 |
| 2001/0021385 A1 | 9/2001 | Volkin et al. |
| 2004/0030516 A1 | 2/2004 | Dunhill et al. |
| 2005/0164929 A1* | 7/2005 | Alvarez et al. ................. 514/12 |
| 2006/0083694 A1* | 4/2006 | Kodas et al. .................... 424/46 |

FOREIGN PATENT DOCUMENTS

| WO | WO0057906 | 10/2000 |
| WO | WO-01/36583 A1 | 5/2001 |
| WO | WO-2004/042012 A2 | 5/2004 |

OTHER PUBLICATIONS

International Search Report and Written Opinion issued for PCT/IB2006/001231, dated Sep. 5, 2006.
Baker, et al., "Rapid Monitoring of Recombinant Protein Products: A Comparison of Current Technologies", Trends in Biotechnology, 20(4):149-156 (2002).
Gracheva, I.M., and Kryvova, A.Y., Enzyme Technology, Textbooks and Manuals for Students of Higher Education Institutions, 2000, p. 121-122, 3rd. Ed., "Elevar" Press, Moscow.

* cited by examiner

*Primary Examiner* — Joseph W Drodge
(74) *Attorney, Agent, or Firm* — Margo H. Furman

(57) ABSTRACT

The addition of buffer to a harvest stream during diafiltration can cause increased turbidity and have other undesirable effects including limiting product recovery. Methods and compositions related to the use of a non-ionic surfactant are provided for improving diafiltration.

19 Claims, No Drawings

SHEAR PROTECTANTS IN HARVEST MICROFILTRATION

CROSS-REFERENCE TO RELATED APPLICATIONS

This application claims priority to provisional U.S. application Ser. No. 60/647,184, filed on Jan. 25, 2005, which is herein incorporated by reference in its entirety.

TECHNICAL FIELD

This application relates to the field of cell culture harvest microfiltration.

BACKGROUND

Diafiltration is used in biotechnological applications for buffer exchange and product recovery, depending on mode of operation. In diafiltration, buffer is introduced into a recycle or retentate tank while filtrate is removed from the system. Diafiltration can be used as a method of washing a retentate that is the product or to wash product through the filtration system for collection. It is a goal of microfiltration harvest processes that use diafiltration to maximize recovery of product from the process stream.

SUMMARY

The invention relates to the discovery that the addition of a non-ionic surfactant, e.g., Pluronic® F68, polyethylene glycol, or other non-ionic block copolymer surfactants, to the buffer used in a diafiltration step as part of a microfiltration process (e.g., tangential flow filtration; TFF) can reduce turbidity of the process fluid. Accordingly the invention comprises a method for diafiltration. The method comprises providing a retentate for diafiltration and adding a non-ionic surfactant to the retentate. The non-ionic surfactant can be, e.g., Pluronic® F68 or polyvinyl alcohol (PVA). In some embodiments, the non-ionic surfactant is in a buffer, e.g., phosphate buffered saline (PBS). The concentration of the non-ionic surfactant in a buffer can be between 0.2 and 4 g/L, 0.2 and 3 g/L, 0.5 and 2.5 g/L, 0.5 and 2 g/L, 0.5 and 1.5 g/L. In some cases the concentration of the non-ionic surfactant in the buffer is about 1 g/L or 2.5 g/L. In certain embodiments, the retentate includes cells and culture medium. In certain aspects of the invention, the turbidity of the filtrate resulting from the diafiltration is reduced compared to the diafiltration performed in the absence of non-ionic surfactant. In another embodiments the recovery of a product from the retentate is increased in the presence of the non-ionic surfactant compared to recovery of the product in the absence of the non-ionic surfactant. In yet another embodiment, the retentate comprises a pharmaceutical product, e.g., a recombinant protein, a recombinant peptide, or a naturally occurring protein or peptide. In some cases, the retentate comprises a buffer isotonic to a cell in the retentate, e.g., PBS. In another embodiment, the diafiltration occurs at a temperature of about 20° C.-25° C., 2° C. to 37° C., or 2° C.-25° C. The diafiltration can be e.g., discontinuous diafiltration or constant volume diafiltration. In certain cases, the concentration of the non-ionic surfactant does not substantially change during diafiltration. The non-ionic surfactant can be in a cell culture medium.

The invention also relates to a product produced using a method, e.g., diafiltration, as described herein.

In another aspect, the invention relates to a method of diafiltration that comprises maintaining a non-ionic surfactant (e.g., Pluronic® F68 or PVA) concentration of about 1 g/L.

In yet another aspect, the invention relates to a composition for diafiltration, the composition comprising about 1 g/L (e.g., Pluronic® F68) or 2.5 g/L (e.g., PVA) of a non-ionic surfactant. The composition can also comprise an isotonic buffer, e.g., PBS.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting.

Other features and advantages of the invention will be apparent from the detailed description, drawings, and from the claims.

DETAILED DESCRIPTION

In protein processing, TFF can be used as part of the recovery process to separate intact cells and debris from other components in the feed stream. For example, a production process that employs cultured cells can use a harvest microfiltration step that incorporates concentration and diafiltration. This process separates cell culture fluid containing a product such as a recombinant protein from the production cell line using, e.g., TFF. Following the initial harvest microfiltration (concentration), the retentate, which generally contains cells at a higher density than the density prior to the initial filtration, is recirculated through a filtering system and diafiltered to recover additional product that is held up in the harvest microfiltration system (diafiltration). For this diafiltration step, an isotonic buffer (e.g., PBS) is generally added to the retentate. This diafiltration can be performed using either a discontinuous or constant volume method for the addition of buffer.

In general, the term "process stream" incorporates the feed stream, permeate stream, and retentate stream, i.e., mobile liquid in the process that contains products of the cell culture. The filtrate is any material that passes through the filter, i.e., the permeate stream. "Retentate" refers to material that does not pass through the filter but encounters the filtration device and is returned to a reservoir. "Feed stream" refers to material that leaves the reservoir, passes through the pump, and feeds the filter.

A goal of procedures such as those described above is to maximize the amount of product, e.g., a secreted protein or peptide product, recovered from the cell culture or retentate, while simultaneously minimizing the amount of undesirable material in the cell culture and process stream. An increase in turbidity load in the cell culture or retentate is generally associated with an increase in the turbidity of the permeate. The undesirable material can include, for example, sub-cellular particulates and debris. In general, turbidity is used as a measure of the load of undesirable material in the process stream. Excessive turbidity in a solution in which cells are suspended, such as culture medium or a buffer or a mixture of both, is undesirable because turbidity indicates conditions that can cause filter blinding, blockage in the clarification train (for example, through pore plugging), and can be detrimental to product quality, including through the release of cellular enzymes. Destruction of cells (e.g., by shear) in the culture being harvested can cause an increase in turbidity of the process stream. As reported herein, it was observed that the addition of buffer to a retentate during diafiltration can increase turbidity, even though the buffer is isotonic.

The invention relates to the discovery that the addition of a buffer (e.g., PBS) containing a non-ionic surfactant (e.g., a non-ionic block copolymer surfactant such as Pluronic® F68 or polyvinyl alcohol (PVA)) decreases the amount of turbidity in the retentate and permeate streams compared to addition of buffer alone to the retentate. In general, turbidity of the retentate is lower in the presence of non-ionic surfactant in a buffer or other solution that is added to the retentate than in the absence of the surfactant. In addition, the turbidity of the filtrate is typically reduced. Typically, the non-ionic surfactant is Pluronic® F68 or PVA. Other non-ionic surfactants that can be used include polyethylene glycol (PEG), for example, PEG having a molecular weight of at least about 1000. Certain compounds that have ionic properties but can function as shear protectants can be used, e.g., dextran. An exemplary concentration of dextran used in the methods described herein is at least 10 g/L. Other suitable compounds can be identified using the methods described herein. The concentration of the non-ionic surfactant or other shear protectant used in the methods described herein is generally between 0.2 g/L and 3 g/L, 0.2 g/L and 4 g/L, 0.5 g/L and 2 g/L, 0.5 g/L and 2.5 g/L, 0.5 g/L and 1.5 g/L, or about 1 g/L. In some cases the concentration of non-ionic surfactant or other shear protectant is at least 1 g/L or at least 1.5 g/L. The maximum amount can be, in some cases, not more than 2 g/L, not more than 5 g/L, or not more than 10 g/L.

In some cases, buffer, e.g., isotonic buffer such as PBS, is added to the retentate prior to commencing TFF. The buffer generally comprises a non-ionic surfactant such as Pluronic® F68.

In an example of the application of the method described herein, a commercial recombinant protein drug substance production process was used that employs a harvest microfiltration step to separate cell culture fluid containing recombinant protein from a production cell line. The harvest system was a Prostak Tangential Flow Filtration (TFF) unit (Millipore, Billerica, Mass.) that included 0.65 μm microfiltration (MF) membrane modules. The whole cell culture fluid (cell-containing) was recirculated through a series of Prostak modules on the retentate side of the TFF system and routed back into the harvest tank. Cell-free culture fluid permeates to the other side of the 0.65 μm Prostak filter module membranes and is collected for further processing.

The whole cell culture fluid was concentrated ten-fold by the initial TFF process. The resulting fluid on the retentate side of the filtration train is referred to herein as the retentate. Following cell concentration, a buffer diafiltration step was performed at 1.8 times the final retentate volume of the microfiltration to improve yield of product held-up in the harvest microfiltration and clarification systems.

The diafiltration buffer used for the harvest scheme was PBS. Other isotonic solutions, e.g., buffers such as Tris buffered saline or growth media can be used in the methods described herein. Non-ionic solutions can also be used. PBS is isotonic and would not be expected to have any detrimental effect on cell viability. However, an undesirable level of turbidity was observed after buffer was added to the retentate. The addition of Pluronic® F68 at a concentration of 1 g/L or PVA at 2.5 g/L to the harvest diafiltration buffer resulted in a reduced turbidity load in the harvest process stream.

Without committing to a particular theory, the reduced turbidity load that is observed when a non-ionic surfactant is used in the recovery process described herein may be due to reduced shear-induced cell destruction during harvest with the non-ionic surfactant acting, at least in part, as a shear protectant.

Advantages of adding a non-ionic surfactant such as Pluronic® F68 or PVA to buffer during diafiltration can be 1) improved product stability in the harvest hold pool, e.g., as a result of lower levels of proteases released from the production cell line during harvesting, 2) reduced cell-derived impurity load in process stream prior to downstream processing, and 3) reduced surface area requirement for the harvest filter train.

Methods of Identifying Useful Non-Ionic Surfactants

Non-ionic surfactants can be tested for their ability to improve the quality of a retentate, for example, by decreasing the amount of undesirable material (e.g., cellular debris) in a harvest stream using methods described herein. Quality can also be determined by assaying the filtrate for, e.g., purity of a product or the quantity of a product recovered in the presence and absence of the use of non-ionic surfactant. In general, a non-ionic surfactant is included in the buffer added during diafiltration such that the retentate contains at least 1%, 5%, 10%, 20%, 50%, 80% (v/v) or more buffer in the retentate. The amount of undesirable material in the retentate is assayed and compared to the amount of undesirable material in retentate diafiltered using the same buffer but without the addition of the non-ionic surfactant. The non-ionic surfactant added with the buffer can be the same or different from a non-ionic surfactant that is in the cell culture medium. In general, the non-ionic surfactant is the same as that in the cell culture medium and the concentration of the surfactant in the buffer is the same as the concentration in the cell culture medium. Various concentrations of a non-ionic surfactant can be assayed to determine a concentration favorable for minimizing the amount of undesirable material in the retentate and maximizing recovery of a product. In some cases, turbidity of the filtrate is assayed in addition to, or instead of, assaying the retentate.

In some embodiments, the turbidity of the retentate is tested after buffer, or buffer containing a non-ionic surfactant, is diafiltered into the retentate. Turbidity provides a measure of sub-cellular particulates and cell debris. In general, lower turbidity is associated with a more desirable quality of retentate. Turbidity can be assayed using methods known in the art. For example, nephelometric methods (Baker et al., Trends Biotechnol. April 2002; 20(4): 149-56) or optical density can be used. Optical density is generally assayed by measuring absorbance: 550 nm-650 nm. Reduced turbidity in the presence of the non-ionic surfactant indicates that the non-ionic surfactant increases the quality of the retentate for TFF. In some cases, various concentrations of a non-ionic surfactant are tested to determine a favorable concentration in a particular process.

Other methods that are known in the art that are used for assaying the quality of a retentate or testing for the presence of cell debris can be used to assess the ability of a non-ionic surfactant to improve the quality of a retentate containing buffer. For example, testing for the intracellular lactate dehydrogenase (LDH) in the retentate and/or permeate can be used as a method of detecting cell lysis. Other methods that can be used include determining the number of cells in a retentate to which buffer has been added. In general, the number of cells in a retentate is assayed in the presence of buffer containing a non-ionic surfactant and in the presence of buffer alone. A useful buffer composition is one in which the total number of cells remains constant in the retentate at end of diafiltration compared to the beginning of diafiltration when diafiltered with buffer containing the non-ionic surfactant. Useful compositions, i.e., buffer plus a non-ionic surfactant, also include buffer compositions for which the total number of cells in the retentate after diafiltration is higher than the number of cells in the retentate after diafiltration using the buffer alone.

The temperature of the diafiltration process can also be adjusted to improve the recovery of product from a retentate, reduce turbidity, reduce filter blinding, or reduce other undesirable qualities of a retentate that contains buffer. In general, diafiltration is carried out at temperatures of, e.g., about 20° C.-25° C., 2° C. to 37° C., or 2° C.-25° C.

Non-limiting examples of products that can be recovered using the methods described herein include proteins and peptides, e.g., antibodies, antibody fragments, recombinant proteins, naturally secreted proteins, proteins and peptides engineered to be secreted, and non-protein products that are produced by a cell.

train through pore plugging and other mechanisms. The addition of the PBS buffer alone may result in a decrease in concentration of shear protectant, effectively by dilution when the buffer is added. Therefore, the cell line is exposed to increased levels of shear in the absence of the shear protectant. Destruction of cells through shear mechanisms in the harvest system can lead to increased process stream turbidity.

The effect of adding a non-ionic surfactant that may act as a shear protectant (e.g., PVA or Pluronic® F68) to the diafiltration buffer is illustrated in Table 1. These studies demonstrate that the final retentate turbidity at the end of diafiltration is 8 to 33 NTU/$10^6$ cells and in the permeate is 2.6 to 4.1 NTU/$10^6$ cells. The harvests in which shear protectant was added to the diafiltration buffer had turbidity in the range 9.7 to 10.1 NTU/$10^6$ cells in the retentate and 0.7 to 2.4 NTU/$10^6$ cells in the permeate. Thus, there is a correlation between the presence of a non-ionic surfactant and a decrease in the retentate turbidity during diafiltration. Permeate turbidity is also decreased.

TABLE 1

Cell number, retentate spun turbidity (1000 rpm for 5 minutes (approximately 201 × g)), and permeate turbidity at the start and end of microfiltration diafiltration. Spun turbidity is a measure of supernatant turbidity after cells are centrifuged from a process sample.

| Batch | Cell number ×$10^6$ | Diafiltration start | | Diafiltration Finish | | Ratio NTU/$10^6$ cells retentate | Ratio NTU/$10^6$ cells permeate | Buffer |
|---|---|---|---|---|---|---|---|---|
| | | Retentate spun turbidity Start | Permeate turbidity Start | Retentate spun turbidity Finish | Permeate turbidity Finish | | | |
| SFP-150-004 R2 | 58.9 | 371 | 9.82 | 1160 | 151 | 19.7 | 2.6 | PBS |
| SFP-150-004 R1 | 55.4 | 918 | 14 | 1836 | 157 | 33.1 | 2.8 | PBS |
| SFP-150-005 R2 | 92.1 | 569 | 9.05 | 739 | 377 | 8.0 | 4.1 | PBS |
| SFP-150-006 R2 | 86.6 | 493 | 6.73 | 874 | 155 | 10.1 | 1.8 | PBS + PVA |
| SFP-150-006 R1 | 120.0 | 546 | 6.47 | 814 | 286 | 6.8 | 2.4 | PBS + Pluronic |
| SFP-150-007 R2 | 82.6 | 381 | 6.33 | 802 | 58.8 | 9.7 | 0.7 | PBS + Pluronic |

EXAMPLES

The invention is further illustrated by the following examples. The examples are provided for illustrative purposes only. They are not to be construed as limiting the scope or content of the invention in any way.

Example 1

Harvest Microfiltration Development

The harvest and clarification process described above was tested using cells producing a recombinant protein. Throughout the cell concentration phase of the microfiltration step, the cells were recirculated in the presence of shear protectant such as PVA (Celvol, Celanese Chemicals, Dallas, Tex.) or Pluronic® F68 (BASF Ludwigshafen, Germany) in the cell culture medium. The turbidity of the permeate (filtrate) remained low under these conditions and the retentate increased in proportion to the increasing cell mass. Turbidity, measured using a nephelometric method, was used to quantify sub-cellular particulate and debris load in the process streams. The addition of the PBS diafiltration buffer (without added non-ionic surfactant) to the retentate resulted in an increase in the turbidity of the retentate and of the permeate.

Excessive turbidity in the permeate stream is undesirable as it can cause filter blinding/blockage in the clarification Example 2

Bench-Scale Model

A study was carried out using a bench-scale model to examine the effect of incorporating a shear protectant into the harvest diafiltration buffer. The model consisted of a cell reservoir from which cells were pumped through a microfiltration tangential flow filtration (MFTFF) device and then returned to the reservoir. Supernatant was removed from the MFTFF device while diafiltration buffer was added to the reservoir allowing a constant volume diafiltration to be performed. For each investigation cells from the same bioreactor and identical test conditions were employed with the only difference being the buffer itself. The buffer was either PBS or PBS containing the shear protectant poly vinyl alcohol (PVA) at a concentration of 2.5 g/L. Turbidity was assayed using the nephelometric method.

In general, the turbidity in the permeate was reduced through the inclusion of PVA in the diafiltration buffer. This is indicated by the measure of permeate stream turbidity normalized to the starting cell concentration prior to diafiltration (Table 2, Tests 1 and 2). A third test (Table 2, Test 3) had a less pronounced effect, with the permeate turbidities being largely equivalent for the PBS and PBS/PVA conditions.

TABLE 2

Diafiltration of cells with PBS or PBS containing PVA

| Test | Diafiltration start VCD ×10⁶ cells/ml | Diafiltration start Permeate turbidity NTU | Diafiltration finish Permeate turbidity NTU | Ratio (permeate) NTU/10⁶ cells/ml | Buffer |
|---|---|---|---|---|---|
| 1a | 55 | 9.1 | 54.5 | 1.0 | PBS |
| 1b | 55 | 12.5 | 40.7 | 0.7 | PBS/PVA |
| 2a | 57 | 13.3 | 77.8 | 1.1 | PBS |
| 2b | 57 | 11.9 | 64.3 | 1.1 | PBS/PVA |
| 3a | 73 | 14.1 | 80.8 | 1.1 | PBS |
| 3b | 73 | 15.1 | 87.3 | 1.2 | PBS/PVA |

An examination of viable cell densities (VCD) and viable cell loss with and without PVA in the diafiltration buffer clearly demonstrates the protective nature of the diafiltration buffer containing PVA (see Table 3). Turbid material generated from this cell loss in Test 3 may well be retained on the retentate side of the filtration device thus not reflecting a marked increase in permeate turbidity. This is possible considering the increased viable cell density at the start of diafiltration, which could change the retention capabilities of the filter, for example through additional cake formation and/or membrane polarization.

The minimization of viable cell loss through inclusion of PVA in all test cases (Tests 1-3) leads to improved filtration properties of the process stream and a reduced risk of filter blinding through pore plugging mechanisms.

TABLE 3

Viable cell densities before and after diafiltration for the Tests 1-3 of Table 2

| Test | Diafiltration start VCD ×10⁶ cells/ml | Diafiltration finish VCD ×10⁶ cells/ml | Viable Cell Loss ×10⁶ cells/ml | Buffer |
|---|---|---|---|---|
| 1a | 55 | 42 | 13 | PBS |
| 1b | 55 | 47 | 8 | PBS/PVA |
| 2a | 57 | 40 | 17 | PBS |
| 2b | 57 | 40 | 14 | PBS/PVA |
| 3a | 73 | 49 | 24 | PBS |
| 3b | 73 | 59 | 14 | PBS/PVA |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for harvesting a product from a cell culture by diafiltration, the method comprising
   (a) providing a retentate for diafiltration, wherein the retentate is a retentate from harvest microfiltration of a cell culture;
   (b) adding a non-ionic surfactant to the retentate; and
   (c) performing diafiltration of the retentate, thereby harvesting a product from a cell culture.

2. The method of claim 1, wherein the non-ionic surfactant is Pluronic® F68.

3. The method of claim 1, wherein the non-ionic surfactant is polyvinyl alcohol (PVA).

4. The method of claim 1, wherein the non-ionic surfactant is in a buffer.

5. The method of claim 1 or claim 2, wherein the non-ionic surfactant is in a buffer and the concentration of the non-ionic surfactant in the buffer is between 0.2 g/L and 4 g/L, 0.2 g/L and 3 g/L, 0.5 g/L and 2.5 g/L, 0.5g/L and 2 g/L, and 0.5 g/L and 1.5 g/L.

6. The method of claim 1 or claim 2, wherein the concentration of the non-ionic surfactant in the buffer is about 1 g/L or 2.5 g/L.

7. The method of claim 1 or claim 2, wherein the retentate comprises cells and culture medium.

8. The method of claim 1 or claim 2, wherein the turbidity of the filtrate resulting from the diafiltration is reduced compared to the diafiltration performed in the absence of non-ionic surfactant.

9. The method of claim 1 or claim 2, wherein the qualitative or quantitative recovery of a product from the retentate is increased in the presence of the non-ionic surfactant compared to recovery of the product in the absence of the non-ionic surfactant.

10. The method of claim 1 or claim 2, wherein the retentate comprises a pharmaceutical product.

11. The method of claim 1 or claim 2, wherein the retentate comprises a recombinant protein.

12. The method of claim 1 or claim 2, wherein the retentate comprises a buffer isotonic to a cell in the retentate.

13. The method of claim 1 or claim 2, wherein the retentate comprises phosphate buffered saline (PBS).

14. The method of claim 1 or claim 2, wherein the diafiltration step occurs at a temperature of about 20° C. to 25° C. 2° C. to 37° C., or 2° C. to 25° C.

15. The method of claim 1, wherein the diafiltration is discontinuous diafiltration.

16. The method of claim 1, wherein the diafiltration is constant volume diafiltration.

17. The method of claim 1, wherein the concentration of the non-ionic surfactant does not substantially change during diafiltration.

18. The method of claim 1, wherein the non-ionic surfactant is in a cell culture medium.

19. The method of claim 17, wherein the concentration of non-ionic surfactant is maintained at about 1 g/L.

* * * * *